United States Patent [19]

Blank et al.

[11] Patent Number: 5,061,487
[45] Date of Patent: Oct. 29, 1991

[54] ANTIMICROBIAL SUPERABSORBENT COMPOSITIONS AND METHODS

[75] Inventors: Lynne M. B. Blank, Brighton, N.Y.; Thomas D. Boyce; William C. White, both of Midland, Mich.

[73] Assignee: Dow Corning Corporation, Midland, Mich.

[21] Appl. No.: 681,582

[22] Filed: Apr. 8, 1991

Related U.S. Application Data

[60] Division of Ser. No. 563,229, Aug. 6, 1990, which is a division of Ser. No. 425,277, Oct. 23, 1989, Pat. No. 4,985,023, which is a continuation-in-part of Ser. No. 191,945, May 9, 1988, Pat. No. 4,990,338.

[51] Int. Cl.$^5$ ............................................. A61K 31/78
[52] U.S. Cl. ...................................... 424/81; 424/430; 424/431; 604/358; 604/372
[58] Field of Search ..................... 424/430, 431, 81; 604/358, 372

[56] References Cited

U.S. PATENT DOCUMENTS

| | | | |
|---|---|---|---|
| 3,804,094 | 4/1974 | Manoussos et al. | 128/290 |
| 3,966,679 | 6/1976 | Gross | 260/47 |
| 4,282,366 | 8/0481 | Eudy | 556/413 |
| 4,394,378 | 7/1983 | Klein | 424/184 |

*Primary Examiner*—Thurman K. Page
*Assistant Examiner*—Louis A. Piccone
*Attorney, Agent, or Firm*—Jim L. DeCesare

[57] ABSTRACT

An antimicrobial superabsorbent composition of a cross-linked hydrophilic sodium salt form of a partially neutralized acrylic acid-based polymer gel having covalently bonded thereto a silane. The composition can be in the form of flakes, strips, powders, filaments, fibers, or films, and may be supplied to a substrate in the form of a coating.

8 Claims, No Drawings

ANTIMICROBIAL SUPERABSORBENT COMPOSITIONS AND METHODS

This application is a division of our prior copending application U.S. Ser. No. 07/563,229, filed Aug. 6, 1990, pending which is a division of U.S. Ser. No. 07/425,277 filed Oct. 23, 1989 now U.S. Pat. No. 4,985,023 issued Jan. 15, 1991 which is in turn a continuation-in-part of our original application U.S. Ser. No. 07/191,945 filed May 9, 1988 U.S. Pat. No. 4,990,338, each of which is assigned to the assignee of the present application.

BACKGROUND OF THE INVENTION

This invention relates to compositions, methods of treatment, and articles of manufacture, wherein there is employed an antimicrobial superabsorbent formed of a cross-linked hydrophilic sodium salt form of a partially neutralized acrylic acid-based polymer gel having covalently bonded thereto a silane, for the purpose of providing the benefits of odor reduction, control of microbes, and reduction of microbial rashes and allergies.

Antimicrobial agents are chemical compositions that are used to prevent microbiological contamination and deterioration of products, materials, and systems Particular areas of application of antimicrobial agents and compositions are, for example, cosmetics, disinfectants, sanitizers, wood preservation, food, animal feed, cooling water, metalworking fluids, hospital and medical uses, plastics and resins, petroleum, pulp and paper, textiles, latex, adhesives, leather and hides, and paint slurries. Of the diverse categories of antimicrobial agents and compositions, quaternary ammonium compounds represent one of the largest of the classes of antimicrobial agents in use. At low concentrations, quaternary ammonium type antimicrobial agents are bacteriostatic, fungistatic, algistatic, sporostatic, and tuberculostatic. At medium concentrations they are bactericidal, fungicidal, algicidal, and viricidal against lipophilic viruses. Silicone quaternary ammonium salt compounds are well known as exemplified by U.S. Pat. No. 3,560,385, and the use of such compounds as antimicrobial agents is taught, for example, in a wide variety of patents such as U.S. Pat. Nos. 3,730,701, and 3,817,739, where the compounds are used to inhibit algae; 3,794,736; 3,860,709; 3,865,728, where the compounds are used to treat aquarium filters 4,259,103; and in British Patent No. 1,386,876. Published unexamined European Application No. 228464 of July 15, 1987, teaches that microorganisms on plants can be killed by the application thereto of an aqueous mixture of a surfactant and an organosilicon quaternary ammonium compound. In a particular application of an antimicrobial silicone quaternary ammonium compound, a paper substrate is rendered resistant to the growth of microorganisms in U.S. Pat. No. 4,282,366. In U.S. Pat. No. 4,504,541, an antimicrobial fabric is disclosed which is resistant to discoloration and yellowing by treatment of the fabric with a quaternary ammonium base containing an organosilicone. U.S. Pat. No. 4,615,937, as well as its companion U.S Pat. No. 4,692,374, relate to wet wiper towelettes having an antimicrobial agent substantive to the fibers of the web and being an organosilicon quaternary ammonium compound. Thus, the versatility of such compositions is readily apparent.

Absorbent polymers capable of absorbing from about thirty to sixty grams of water per gram of polymer are known, as is the use of such polymers in disposable diapers, sanitary napkins, surgical pads, and bath mats for example. Particularly sought-after property is increased water absorbency polymers having this property often are referred to as hydrogels or superabsorbents. The nature and utility of superabsorbents are illustrated by U.S Pat. No. 4,449,977. According to this reference, a desirable feature of a superabsorbent is the presence of acrylate or methacrylate groups which can be salts, amides, esters, or the free acids. Many hydrogels are based on acrylate and methacrylate polymers and copolymers, for example, as shown in U.S. Pat. Nos. 2,976,576, 3,220,960, 3,993,616, 4,154,898, 4,167,464, 4,192,727, 4,192,827, and 4,529,739. Hydrogels based on starch or a modified starch are shown by U.S. Pat. Nos. 4,069,177, 4,076,663, 4,115,332, and 4,117,222. Other hydrogels are based on poly(oxyalkylene) glycols as in U.S. Pat. No. 3,783,872. Hydrogels prepared from hydrolyzed crosslinked polyacrylamides and crosslinked sulfonated polystyrenes are described in U.S. Pat. No. 4,235,237. Finally, polymers based on maleic anhydride have been described in U.S. Pat. Nos. 2,988,539, 3,393,168, 3,514,419, 3,557,067, and 4,401,793. U.S. Pat. No. 3,900,378 describes hydrogels from radiation crosslinked blends of hydrophilic polymers and fillers. Such category of absorbent polymers preferred in the present invention, however, can be exemplified by, for example, U.S. Pat. No. 3,966,679, which relates to acrylic acid based water swellable super absorbent polymers useful as catamenial tampons and diapers. Such absorbent polymers that possess, in addition to their superabsorbency characteristics, the property of antimicrobial activity, are not known, however. Therefore, in accordance with the present invention, it has been found that superabsorbent compositions which have antimicrobial properties can be formed, which possess the characteristics and advantages of both categories of the silicone quaternary ammonium salts as well as the acrylic acid based water swellable super absorbent polymer compositions noted above. Thus, in addition to absorbing large quantities of fluids, the compositions of the present invention act in preventing microbiological contamination and deterioration of products, materials, and systems. For example, 3-(trimethoxysilyl)propyldimethyloctadecylammonium chloride, hereinafter referred to as TMS, is an effective antimicrobial agent in which the active ingredient hydrolyzes in water and reacts with substrates with which it is brought into contact. These substrates demonstrate nonleaching broad spectrum antimicrobial activity. By including an antimicrobial component in the water swellable absorbent composition the benefits of both compositions are realized as against both functioning independently one from the other. Hence the compositions set forth in the present invention possess unique features and advantages over existing antimicrobial treating agents and hydrophilic gels and provide improved results thereover. Thus, the disadvantages of the prior art are overcome with the present invention wherein improved antimicrobial agents are provided.

SUMMARY OF THE INVENTION

This invention relates to an antimicrobial superabsorbent composition of a cross-linked hydrophilic sodium salt form of a partially neutralized acrylic acid-based polymer gel having covalently bonded thereto a silane of the general formula

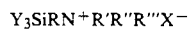

where Y denotes a hydrolyzable radical, R denotes a divalent hydrocarbon radical with 1 to 6 carbon atoms, R', R" and R'" independently denote saturated or unsaturated hydrocarbon radicals containing 1 to 18 carbon atoms, saturated or unsaturated organic radicals consisting of carbon, hydrogen and oxygen; carbon, hydrogen, and sulfur; or carbon, hydrogen and nitrogen, and X denotes an anion.

The silane can also be represented by the general formula $$Y_3Si(CH_2)_mN^+(CH_3)_2(CH_2)_nCH_3X^-$$

Y denotes a hydrolyzable radical, X denotes an acid anion, and where m+n is 16 to 23, m is 1 to 11, and n is 9 to 17. Specific examples of compounds included thereunder are, for example, the silane represented by the formula $$(CH_3O)_3Si(CH_2)_3N^+(CH_3)_2C_{18}H_{37}Cl^-$$

and the silane represented by the formula $$(CH_3O)_3Si(CH_2)_3N^+(C_{10}H_{21})_2(CH_3)Cl^-$$

The invention also relates to a method of inhibiting the proliferation of potentially destructive microorganisms on a substrate by treating the substrate with an effective amount of an antimicrobial superabsorbent composition formed of a cross-linked hydrophilic sodium salt form of a partially neutralized acrylic acid-based polymer gel having covalently bonded thereto a silane of the general formula $$Y_3SiRN^+R'R''R'''X^-$$

where Y denotes a hydrolyzable radical, R denotes a divalent hydrocarbon radical with 1 to 6 carbon atoms R', R" and R'" independently denote saturated or unsaturated hydrocarbon radicals containing 1 to 18 carbon atoms, saturated or unsaturated organic radicals consisting of carbon, hydrogen and oxygen; carbon, hydrogen, and sulfur; or carbon, hydrogen and nitrogen, and X denotes an anion. The composition can be in the form of flakes, strips, powders, filaments, fibers, or films.

The invention further relates to a method of reducing odor and simultaneously controlling diaper rash by the suppression of bacteria that attack urinary urea with the liberation of ammonia by impregnating the diaper fabric with an effective amount of a composition for controlling the spread of infection, the composition being an antimicrobial superabsorbent formed of a cross-linked hydrophilic sodium salt form of a partially neutralized acrylic acid-based polymer gel having covalently bonded thereto a silane of the general formula $$Y_3SiRN^+R'R''R'''X^-$$

where Y denotes a hydrolyzable radical, R denotes a divalent hydrocarbon radical with 1 to 6 carbon atoms, R', R" and R'" independently denote saturated or unsaturated hydrocarbon radicals containing 1 to 18 carbon atoms saturated or unsaturated organic radicals consisting of carbon, hydrogen and oxygen; carbon, hydrogen, and sulfur; or carbon, hydrogen and nitrogen, and X denotes an anion.

It is therefore an object of the present invention to provide compositions, methods of treatment, and articles of manufacture, wherein there is employed an antimicrobial superabsorbent formed of a cross linked hydrophilic sodium salt form of a partially neutralized acrylic acid-based polymer gel having covalently bonded thereto a silane.

It is also an object of the present invention to provide compositions, methods of treatment, and articles of manufacture, wherein there is employed an antimicrobial superabsorbent formed of a cross linked hydrophilic sodium salt form of a partially neutralized acrylic acid-based polymer gel having covalently bonded thereto a silane for the purpose of providing the benefits of odor reduction, control of microbes, and reduction of microbial rashes and allergies.

These and other features, objects, and advantages, of the present invention will become apparent from the following detailed description of the invention.

DETAILED DESCRIPTION OF THE INVENTION

The compositions of the present invention were prepared in accordance with the Examples set forth hereinbelow, and in the Examples as well as in the Tables tabulating results thereof, the composition identified as TMS refers to a product manufactured by the Dow Corning Corporation as an antimicrobial agent and is 3-(trimethoxysilyl)-propyloctadecyldimethyl ammonium chloride diluted to forty-two percent active ingredients by weight with methanol, and having the formula $$(CH_3O)_3Si(CH_2)_3N^+(CH_3)_2C_{18}H_{37}Cl^-$$

The material DRYTECH® is a product manufactured by the Dow Chemical Company and is a water swellable absorbent of a carboxylic polyelectrolyte. This cross-linked hydrophilic sodium salt form of a partially neutralized acrylic acid based polymer gel can be prepared by the techniques described for example, in U.S. Pat. No. 3,966,679, issued June 29, 1976, to James R. Gross, and assigned to the Dow Chemical Company. The materials DRYTECH® and TMS are otherwise combined and reacted together in order to form a covalent bond therebetween.

The polymeric material DRYTECH® absorbs and holds large amounts of water in a gel-like matrix. This gel, however, is an ideal situs for microorganisms when some type of nutrient is Supplied. For example, in diapers and sanitary pads, fluids are absorbed which contain heavy organic loads of potential nutrients resulting in an ideal environment for microbial growth. This can be offset by incorporating into the absorbent polymer in a covalent bonding relationship an antimicrobial agent such as TMS thereby producing an otherwise antimicrobial superabsorbent. The antimicrobial agent can be incorporated by addition of the agent to the absorbent polymer during its manufacture, or by addition of the agent to the absorbent polymer following its manufacture as a treated filler or by a non-aqueous treatment of the absorbent polymer with the agent in toluene. It has been found that even though the antimicrobial agent may be classified as a hydrophobing agent, it does not function in the fashion of reducing the absorbent capacity of the polymer. In fact, the gel strength of the absorbent polymer as well as its salt tolerance are improved. In diapers and sanitary pads containing the compositions of the present invention, it has been found that such items possess the added benefits of reduced odor, improved control of microbes, and the reduction of microbial rashes and allergies.

The anion of an aqueous sodium salt of bromophenol blue can be complexed with the cation of a polymerized silane of this invention while it is on a substrate. The blue colored complex, substantive to a water rinse, is qualitatively indicative of the presence of the cation on the substrate thus indicating the extent of antimicrobial agent on a given substrate. A comparison of the intensity of retained blue color to a color standard is used as a check to determine if the treatment has been applied properly.

The method consists of preparing a 0.02 to 0.04 weight percent solution of bromophenol blue in distilled water. This solution is made alkaline using a few drops of saturated $Na_2CO_3$ solution per 100 milliliters of the solution. Two to three drops of this solution are placed on the treated substrate and allowed to stand for two minutes. The substrate is then rinsed with copious amounts of tap water and the substrate is observed for a blue stain and it is compared to a color standard.

For a spectrophotometric determination, the following test is used.

The sodium salt of bromophenol blue is depleted from a standard solution by complexing with the cations on a treated substrate. The change in bromophenol blue concentration is determined spectrophotometrically or by comparison with color standards whereby the level of substrate treatment by the cationic silane is determinable.

The method consists of preparing a 0.02 weight percent standard solution of bromophenol blue in distilled water. It is made alkaline with a few drops of saturated $Na_2CO_3$ solution per 100 milliliters of bromophenol blue solution. The color of this solution is purple.

The blank solution is adjusted to yield a 10 to 12% transmittance reading when measured in 1 cm cells using a spectrophotometer set at 589 nm by the following method.

Fill a container ¾ full of distilled water and add 2 ml of the 0.02% standard bromophenol blue solution for every 50 ml of distilled water. Add 0.5 ml of a 1% Triton ® X-100 surfactant (manufactured by Rohm and Haas, Philadelphia, Pa., USA) aqueous solution for every 50 ml of water. Mix, and using the spectrophotometer, determine the maximum absorbance. Adjust the upper zero to 100% transmittance with distilled water. Check the percent transmittance of the working bromophenol blue solution at the maximum absorbance setting. Adjust the blank solution to 10 to 12% transmittance with either water or bromophenol blue standard solution as necessary.

The samples of treated substrate are tested by placing 0.5 gram samples of the substrate standards in a flask large enough for substantial agitation of the sample and the test solution. Add 50 ml of the working solution. Agitate for 20 minutes on a wrist-action shaker. Fill the test curvette with the test solution. Centrifuge if particulate matter is present. Measure the % transmittance at the wavelength set forth above. The transmittance is compared against a standard curve prepared by preparing several substrate samples of known concentration of the cationic silane. For example samples containing a known amount of cationic silane at for example 0%, 0.25%, 0.50%, 0.75% and 1% are read spectrophotometrically and a curve is plotted.

The silanes useful in this invention also have the general formula

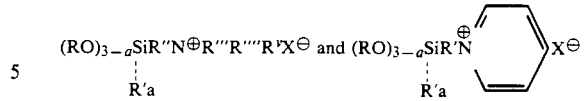

It should be noted that generically, these materials are quaternary ammonium salts of silanes. Most of the silanes falling within the scope of this invention are known silanes and references disclosing such silanes are numerous. One such reference U.S. Pat. No. 4,259,103, issued to James R. Malek and John L. Speier, on Mar. 31 1981, discusses the use of such silanes to render the surfaces of certain substrates antimicrobial. Canadian Patent No. 1,010,782, issued to Charles A. Roth shows the use of fillers treated with certain silanes to be used in paints and the like to give antimicrobial effects.

Numerous other publications have disclosed such silanes, namely, A. J. Isquith, E. A. Abbott and P. A. Walters, Applied Microbiology, December, 1972, pages 859-863; P. A. Walters, E. A. Abbott and A. J. Isquith, Applied Microbiology, 25, No. 2, p. 253-256, February 1973 and E. A. Abbott and A. J. Isquith U.S. Pat. No. 3,794,736 issued Feb. 26, 1974, U.S. Pat. No. 4,406,892, issued Sept. 27, 1983 among others.

For purposes of this invention, the silanes can be used neat or they can be used in solvent or aqueous-solvent solutions. When the silanes are used neat, the inventive process is preferably carried out in a system in which some small amount of water is present. If it is not possible to have s system with some small amount of water present, then a water soluble or water-dispersable, low molecular weight hydrolyzate of the silane may be used. What is important is the fact that the durability of any effect produced by the silane as part of a product requires that the silane molecule react with a surface to a certain extent. The most reactive species, as far as the silanes are concerned is the $\equiv$SiOH that is formed by hydrolysis of the alkoxy groups present on the silane. The $\equiv$SiOH groups tend to react with the surface and bind the silanes to the surface. It is believed by the inventor even though the prime mode of coupling to the surface system is by the route described above, it is also believed by the inventor that the alkoxy groups on the silicon atom may also participate in their own right to bind to the surface.

Preferred for this invention is a reactive surface containing some small amount of water. By "reactive", it is meant that the surface must contain some groups which will react with some of the silanols generated by hydrolysis of the silanes of this invention.

R in the silanes of this invention are alkyl groups of 1 to 4 carbon atoms. Thus, useful as R in this invention are the methyl, ethyl, propyl and butyl radicals. R can also be hydrogen thus indicating the silanol form, i.e. the hydrolyzate. The value of a is 0, 1 or 2 and R′ is a methyl or ethyl radical.

R″ for purposes of this invention is an alkylene group of 1 to 4 carbon atoms. Thus, R″ can be alkylene groups such as methylene, ethylene, propylene, and butylene. R‴, R⁗, and $R^v$ are each independently selected from a group which consists of alkyl radicals of 1 to 18 carbons, $-CH_2C_6H_5$, $-CH_2CH_2OH$, $-CH_2OH$, and $-(CH_2)_xNHC(O)R^{vi}$. x has a value of from 2 to 10 and $R^{vi}$ is a perfluoroalkyl radical having a formula from 1 to 12 carbon atoms. X is chloride, bromide, fluoride, iodide, acetate or tosylate.

Preferred for this invention are the silanes of the general formula

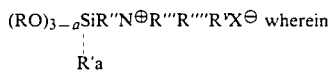

$(RO)_{3-a}SiR''N^{\oplus}R'''R''''R^vX^{\ominus}$ wherein
 $\quad\quad\quad\quad\quad\quad |$
 $\quad\quad\quad\quad\quad\quad R'_a$ R is methyl or ethyl; a has a value of zero; R" is propylene; R''' is methyl or ethyl; R'''' and R$^v$ are selected from alkyl groups containing 1 to 18 carbon atoms wherein at least one such group is larger than eight carbon atoms and x is either chloride, acetate or tosylate.

Most preferred for this invention are those silanes having the formula $(CH_3O)_3Si(CH_2)_3N^{\oplus}(CH_3)_2C_{18}H_{37}Cl^-$ and
$(CH_3O)_3Si(CH_2)_3N^{\oplus}CH_3(C_{10}H_{21})_2Cl^-$.

As indicated above, most of these silanes are known from the literature and methods for their preparation are known as well. See, for example, U.S. Pat. No. 4,282,366, issued Aug. 4, 1981; U.S. Pat. No. 4,394,378, issued July 19, 1983, and U.S. Pat. No. 3,661,963, issued May 9, 1972, among others.

Specific silanes within the scope of the invention are represented by the formulas:

$(CH_3O)_3Si(CH_2)_3N^+(CH_3)_2C_{18}H_{37}Cl^-$, $(CH_3O)_3Si(CH_2)_3N^+(CH_3)_2C_{18}H_{37}Br^-$, $(CH_3O)_3Si(CH_2)_3N^+(C_{10}H_{21})_2CH_3Cl^-$, $(CH_3O)_3Si(CH_2)_3N^+(C_{10}H_{21})_2CH_3BR^-$, $(CH_3O)_3Si(CH_2)_3N^+(CH_3)_3Cl^-$, $(CH_3O)_3SiCH_2CH_2CH_2P^+(C_6H_5)_3Cl^-$, $(CH_3O)_3SiCH_2CH_2CH_2P^+(C_6H_5)_3Br^-$, $(CH_3O)_3SiCH_2CH_2CH_2P^+(CH_3)_3Cl^-$, $(CH_3O)_3SiCH_2CH_2CH_2P^+(C_6H_{13})_3Cl^-$, $(CH_3O)_3Si(CH_2)_3N^+(CH_3)_2C_4H_9Cl^-$, $(C_2H_5O)_3Si(CH_2)_3N^+(CH_3)_2C_{18}H_{37}Cl^-$, $(CH_3O)_3Si(CH_2)_3N^+(CH_3)_2CH_2C_6H_5Cl^-$, $(CH_3O)_3Si(CH_2)_3N^+(CH_3)_2CH_2CH_2OHCl^-$,

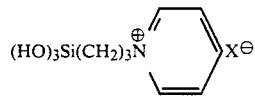

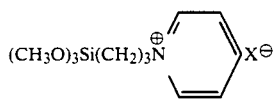

$(CH_3O)_3Si(CH_2)_3N^+(CH_3)_2(CH_2)_3NHC(O)(CF_2)_6CF_3Cl^-$, $(CH_3O)_3Si(CH_2)_3N^+(C_2H_5)_3Cl^-$.

X is chlorine in the above structures.

The compositions of the present invention have a wide range of application including, for example but not limited to, bandages, surgical tampons, sorptive dental rolls, catamenial tampons, sanitary napkins, diapers, body urinals, underarm perspiration pads, breast pads, disposable hat bands, disposable wiping cloths, tissue wipes, pre-moistened towelettes, mattress pads, undersheets, dressings, facial tissues, and of woven or unwoven materials and fabrics such as cotton, cloth, rayon, nylon, wool, surgical gauze, burlap, or paper.

EXAMPLE I

A mixture of five percent by weight of treated CAB-O-SIL ® and ninety-five percent by weight of DRYTECH ® was prepared by combining in a container 19.17 grams of DRYTECH ® and 1.0 grams of CAB-O-SIL ® pre-treated with one percent by weight of TMS. The material CAB-O-SIL ® is colloidal silica particles manufactured by Cabot Corporation, Kokomo, Ind. The ingredients were thoroughly mixed together in the container, and blended with a magnetic stirrer on a hot plate set at low heat while maintaining agitation for thirty minutes. The product from the container was allowed to cool and gravity filtered, and allowed to dry overnight at room temperature. The resulting powder in an amount of 0.5 grams was placed in fifty milliliters of bromophenol blue standard solution and agitated for about twenty minutes. Observations were made based on color, and the color was found to be purple-blue. The gel was dried to remove moisture, and the powder was rinsed with toluene to determine if the treatment was durable. No purple-blue color was found to have been removed by the toluene indicating that the treatment was durable.

EXAMPLE II

A mixture of ten percent by weight of treated CAB-O-SIL ® and ninety percent by weight of DRYTECH ® was prepared by combining in a container 22.5 grams of DRYTECH ® and 2.5 grams of CAB-O-SIL ® pre-treated with one percent by weight of TMS. The ingredients were thoroughly mixed together in the container, and blended with a magnetic stirrer on a hot plate set at low heat while maintaining agitation for thirty minutes. The product from the container was allowed to cool and gravity filtered, and allowed to dry overnight at room temperature. The resulting powder in an amount of 0.5 grams was placed in fifty milliliters of bromophenol blue standard solution and agitated for about twenty minutes. Observations were made based on color, and the color was found to be blue. The gel was dried to remove moisture, and the powder was rinsed with toluene to determine if the treatment was durable. No blue color was found to have been removed by the toluene indicating that the treatment was durable.

EXAMPLE III

A mixture of five percent by weight of treated aluminum chlorohydrate and ninety-five percent by weight of DRYTECH ® was prepared by combining in a container 19.06 grams of DRYTECH ® and 2.12 grams of aluminum chlorohydrate pre-treated with one percent by weight of TMS. The ingredients were thoroughly mixed together in the container, and blended with a magnetic stirrer on a hot plate set at low heat while maintaining agitation for thirty minutes. The product from the container was allowed to cool and gravity filtered, and allowed to dry overnight at room temperature. The resulting powder in an amount of 0.5 grams was placed in fifty milliliters of bromophenol blue standard solution and agitated for about twenty minutes. Observations were made based on color, and the color was found to be purple.

EXAMPLE IV

A mixture was prepared by combining in a container 134.44 grams of toluene, 19.34 grams of DRYTECH ®, and 2.42 grams of TMS. The ingredients were thoroughly mixed together in the container, and blended with a magnetic stirrer on a hot plate set at low heat while maintaining agitation for thirty minutes. The product from the container was allowed to cool and gravity filtered, and allowed to dry overnight at room temperature. The resulting powder in an amount of 0.5 grams was placed in fifty milliliters of bromophenol blue standard solution and agitated for about twenty minutes. Observations were made based on color, and the color was found to be blue. The powder was dried, rinsed with toluene and found durable as in Example II.

EXAMPLE V

A mixture was prepared by combining in a container 134.44 grams of Toluene, 20.0 grams of DRYTECH ®, and 0.125 grams of TMS. The ingredients were thoroughly mixed together in the container, and blended with a magnetic stirrer on a hot plate set at low heat while maintaining agitation for thirty minutes. The product from the container Was allowed to cool and gravity filtered, and allowed to dry overnight at room temperature. The resulting powder in an amount of 0.5 grams was placed in fifty milliliters of bromophenol blue standard solution and agitated for about twenty minutes. Observations were made based on color and the color was found to be purple-blue. The gel was dried to remove moisture and the powder was rinsed with toluene to determine if the treatment was durable as to the absorbent polymer. No purple-blue color was found to have been removed by the toluene indicating that the treatment was durable.

EXAMPLE VI

A mixture was prepared by combining in a container 134.44 grams of Toluene, 20.0 grams of DRYTECH ®, and 2.5 grams of TMS. The ingredients were thoroughly mixed together in the container, and blended with a magnetic stirrer on a hot plate set at low heat while maintaining agitation for thirty minutes. The product from the container was allowed to cool and gravity filtered, and allowed to dry overnight at room temperature. The resulting powder in an amount of 0.5 grams was placed in fifty milliliters of bromophenol blue standard solution and agitated for about twenty minutes. Observations were made based on color, and the color was found to be blue. The gel was dried to remove moisture, and the powder was rinsed with toluene to determine if the treatment was durable as to the absorbent polymer No blue color was found to have been removed by the toluene indicating that the treatment was durable.

EXAMPLE VII

A mixture was prepared by combining in a container 134.44 grams of Toluene, 20.0 grams of DRYTECH ®, and 5.0 grams of TMS. The ingredients were thoroughly mixed together in the container and blended with a magnetic stirrer on a hot plate set at low heat while maintaining agitation for thirty minutes the product from the container was allowed to cool and gravity filtered, and allowed to dry overnight at room temperature. The resulting powder in an amount of 0 5 grams was placed in fifty milliliters of bromophenol blue standard solution and agitated for about twenty minutes. Observations were made based on color, and the color Was found to be blue. The gel was dried to remove moisture, and the powder was rinsed with toluene to determine if the treatment was durable as to the absorbent polymer. No blue color was found to have been removed by the toluene indicating that the treatment was durable.

A control sample of DRYTECH ® when treated alone in accordance with the foregoing procedures rendered a purple color.

TABLE I

| EXAMPLE | DRYTECH ® | CAB-O-SIL ® | TMS | COLOR |
|---------|-----------|-------------|-----|-------|
| 1 | * | *D | * | purple-blue |
| 2 | * | *D | * | blue |
| 3 | * | A, D | * | purple |
| 4 | *B, D | C | * | blue |
| 5 | *B, D | C | * | purple-blue |
| 6 | *B, D | C | * | blue |
| 7 | *B, D | C | * | blue |
| Control | C | C | C | purple |

A = CAB-O-SIL ® replaced with aluminum chlorohydrate.
B = Toluene treated.
C = No ingredient included.
D = TMS durable bound.
Control = DRYTECH ®
*Ingredient included.

A consideration of the foregoing results of the treated materials by bromophenol blue analytical analysis tabulated and set forth in Table I indicates that the treatments with the antimicrobial agent in Examples 2, 4, 6, and 7, were highly effective as evidenced by the blue color; that the treatments with the antimicrobial agent in Examples 1 and 5 were moderately effective as evidenced by the purple-blue color; and that the treatment evidencing a purple color was of little or no effect, including the control sample.

The antimicrobial activity of a treated surface is evaluated by shaking a sample weighing 0.75 grams in a 750,000 to 1,500,000 count *Klebsiella pneumoniae* suspension for a one hour contact time. The suspension is serially diluted both before and after contact, and cultured. The number of viable organisms in the suspensions is determined. The percent reduction based on the original count is determined. The method is intended for those surfaces having a reduction capability of 75 to 100% for the specified contact time. The results are reported as the percent reduction.

Media used in this test are nutrient broth, catalog No. 0003-01-6 and tryptone glucose extract agar, catalog No 0002-01-7 both available from Difco Laboratories, Detroit, Mich. U.S.A. The microorganism used is *Klebsiella pneumoniae* American Type Culture Collection; Rockville, Md. U.S.A., catalog No. 4352.

The procedure used for determining the zero contact time counts is carried out by utilizing two sterile 250 ml. screw-cap Erlenmeyer flasks for each sample. To each flask is added 70 ml of sterile buffer solution. To each flask is added, aseptically, 5 ml of the organism inoculum. The flasks are capped and placed on a wrist action shaker. They are shaken at maximum speed for 1 minute. Each flask is considered to be at zero contact time and is immediately subsampled by transferring 1 ml of each solution to a separate test tube containing 9 ml of sterile buffer The tubes are agitated with a vortex mixer and then 1 ml of each solution is transferred to a second test tube containing 9 ml of sterile buffer. Then, after agitation of the tubes 1 ml of each tube is transferred to a separate sterile petri dish. Duplicates are also prepared. Sixteen ml of molten (42° C.) tryptone glucose extract agar is added to each dish. The dishes are each rotated ten times clockwise and ten times counterclockwise. The dishes are then incubated at 37° C. for 24 to 36 hours. The colonies are counted considering only those between 30 and 300 count as significant. Duplicate samples are averaged. The procedure used for determining the bacterial count after 1 hour is essentially the same as that used to determine the count at the zero contact time. The only difference is that pour plating is performed at the 10° and $10^{-1}$ dilutions as well as at the $10^{-2}$ dilution. "Percent reduction" is calculated by the formula $$\% R = \frac{\frac{B+C}{2} - A}{\frac{B+C}{2}} 100$$

where A is the count per milliliter for the flask containing the treated substrate; B is zero contact time count per milliliter for the flask used to determine "A" before the addition of the treated substrate and C is zero contact time count per milliliter for the untreated control substrate.

The microbiological efficacy of the compositions of the present invention was determined as noted above. The antimicrobial activity of treated surfaces of the compositions was, however, evaluated by shaking samples in a 750,000 to 1,500,000 count *Escherichia coli* and *Klebsiella pneumoniae* suspension for a one hour contact time. The suspension was serially diluted both before and after contact and cultured. The number of viable organisms in the suspensions was determined. The percent reduction based on the original count was also determined. The results and data of the antimicrobial activity dynamic surface testing conducted are set forth in the Tables II and III hereinbelow and indicating that the compositions are antimicrobially active in their nature and function, in addition to performing as superabsorbent materials, and that the microorganisms were substantially reduced in number. Accordingly, the antimicrobial activity of the compositions of the present invention was rated excellent.

In the Tables, the growth was rated from (−) for no growth, (+) for 1-100 colonies, (++) for 100-300 colonies, and (+++) for colonies too numerous to count. The test system employed consisted of seventy-five milliliters of diluent pre-inoculated with approximately 15,000 CFU per milliliter. Samples to be tested were added at the rate of one-half of one gram per seventy-five milliliters. Standardized sub-samples were prepared with a sterile swab and plated on TGE agar.

TABLE II

| | *ESCHERICHIA COLI* PHOSPHATE BUFFER | | |
|---|---|---|---|
| | TIME IN HOURS | | |
| SAMPLE | 0 | 1 | 24 |
| 4 | +++ | +++ | +++ |
| 5 | +++ | +++ | +++ |
| 6 | +++ | +++ | ++ |
| 7 | +++ | +++ | + |
| Control | +++ | +++ | +++ |

TABLE II-continued

| | *ESCHERICHIA COLI* PHOSPHATE BUFFER | | |
|---|---|---|---|
| | TIME IN HOURS | | |
| SAMPLE | 0 | 1 | 24 |
| TMS | +++ | +++ | + |

TABLE III

| | *KLEBSIELLA PNEUMONIAE* | | | | | |
|---|---|---|---|---|---|---|
| | PHOSPHATE BUFFER TIME IN HOURS | | | 0.85% SALINE TIME IN HOURS | | |
| SAMPLE | 0 | 1 | 24 | 0 | 1 | 24 |
| 4 | +++ | +++ | +++ | +++ | +++ | +++ |
| 5 | +++ | +++ | + | +++ | +++ | +++ |
| 6 | +++ | +++ | + | +++ | +++ | + |
| 7 | +++ | +++ | + | +++ | +++ | + |
| Control | +++ | +++ | +++ | +++ | +++ | +++ |
| TMS | +++ | + | + | +++ | +++ | + |

The following example illustrates a further concept of the present invention in which it can be seen that the treatment of the absorbent polymer gel with the organosilane not only does not prevent hydrophobing and reduction of the absorbent capacity of the polymer gel, but can in fact be used to vary the rate at which the polymer gel absorbs a fluid with respect to time.

EXAMPLE VIII

Samples were prepared by taking polymer gel of approximately 25 weight percent solids and 75 weight percent water and mixing with 0.25 weight percent TMS. The resulting mix was dried at 110° C. for 12 hours and the resulting solid mass was ground and screened to 20-160 mesh particles. The sample was a homogenous blend of the gel and TMS.

Another sample was prepared with a surface treatment A 100 ml water mixture composed of 10% by volume of TMS and 90% by volume water was prepared. A 5 gram sample of polymer gel was placed in the mixture for five minutes, and the resulting sample was dried at 110° C. and ground to 20-160 mesh particles.

Both samples were tested against a control sample of polymer gel on a gravimetric absorbing test device. The device allows water to be measured with the natural absorbent force or isometric pressure producing the driving force for uptake. The results are shown in TABLE IV.

TABLE IV

| Time | Control (%) | Blended 0.25 TMS | 90% TMS + 10% water surface treatment |
|---|---|---|---|
| 1 min | 8.45 | 6.40 | 5.77 |
| 2 min | 11.45 | 8.95 | 8.83 |
| 3 min | 12.73 | 10.89 | 11.28 |
| 4 min | 13.37 | 12.10 | 12.26 |
| 5 min | 13.83 | 12.84 | 13.06 |
| 10 min | 14.91 | 14.59 | 14.59 |
| 20 min | 16.01 | 16.36 | 16.40 |

In Table IV, it is noted that all tests were made with 0.2 grams of sample sandwiched between two pieces of No. 1 Whatman filter paper. The data clearly indicate a delay in the rate of uptake in the initial few minutes, and it should be pointed out that the treatment of the polymer gel with the organosilane did not affect the overall equilibrium absorption capacity of the polymer gel after the elapse of some twenty minutes. The blended column of data is equivalent to a treatment level of about one percent by weight of TMS based on the total dry weight of the composition whereas the surface treatment column of data is equivalent to a treatment level of one hundred-ninety percent by weight of TMS based on the total dry weight of the composition. The variable uptake and controlled rate of absorption exhibited in Table IV has application in composite articles containing more than a single absorbent strata. For example, a diaper containing an inner layer of quickly absorbent untreated polymer gel surrounded by a layer of slowly absorbent organosilane treated polymer gel, would absorb fluids by a differential rate of absorption in which fluid migration initially would be to the inner more quickly absorbent layer as a function of time, as evident from the data in Table IV. This differential in the rate of absorbency and in the driving force is due to the difference in the absorbent capacities of the two layers as exemplified by the data in the control column and in the treated columns in Table IV, respectively. While a composite absorbent diaper has been used to illustrate this concept, the mechanism would be equally applicable to the other types of composite articles such as body fluid absorbents including wound and surgical dressings, tampons, hygiene pads, sweat pads, and devices for absorbing waste spills of toxic wastes for example.

It will be apparent from the foregoing that many other variations and modifications may be made in the structures, compounds, compositions, articles of manufacture and methods described herein without departing substantially from the essential features and concepts of the present invention. Accordingly, it should be clearly understood that the forms of the invention described herein are exemplary only and are not intended as limitations on the scope of the present invention.

That which is claimed is:

1. A catamenial tampon comprising an outer layer of an organosilane treated polymer gel, and an inner layer of the polymer gel which is free of the organosilane, the rate at which the outer layer of the organosilane treated polymer gel absorbs a fluid with respect to time being slower than the rate at which the inner layer of the polymer gel which is free of the organosilane absorbs a fluid with respect to time, whereby there is established a differential rate of absorption between the inner layer and the outer layer as a function of time causing initial fluid migration to the inner layer, the polymer gel being a water absorbing crosslinked hydrophilic sodium salt form of a partially neutralized acrylic acid-based polymer gel, and the organosilane having an formula selected from the group consisting of

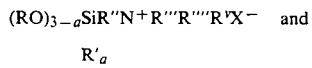

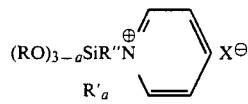

wherein in each formula
R is an alkyl radical of 1 to 4 carbon atoms or hydrogen;
a has a value of 0, 1 or 2;
R' is a methyl or ethyl radical;
R" is an alkylene group of 1 to 4 carbon atoms;
R''', R'''' and R$^v$ are each independently selected from the group consisting of alkyl radicals of 1 to 18 carbon atoms, —CH$_2$C$_6$H$_5$, —CH$_2$CH$_2$OH, —CH$_2$OH, and —(CH$_2$)$_x$NHC(O)R$^{vi}$, wherein x has a value of from 2 to 10 and R$^{vi}$ is a perfluoroalkyl radical having from 1 to 12 carbon atoms; and X is chloride, bromide, fluoride, iodide, acetate, or tosylate.

2. The tampon of claim 1 wherein the organosilane is 3-(trimethoxysilyl) propyldimethyloctadecyl ammonium chloride of the formula

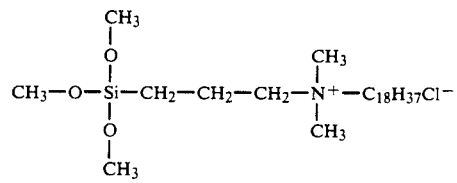

3. The tampon of claim 1 in which the polymer gel is in a form selected from the group consisting of flakes, strips, powders, filament, or fibers.

4. The tampon of claim 1 in which the organosilane is present in the outer layer at a level of about ninety percent by weight based on the total weight of the outer layer.

5. A catamenial tampon which includes at least one layer of an organosilane treated polymer gel, and at least one layer of the polymer gel which is free of the organosilane, the polymer gel being a water absorbing crosslinked hydrophilic sodium salt form of a partially neutralized acrylic acid-based polymer gel, and the organosilane having a formula selected from the group consisting of

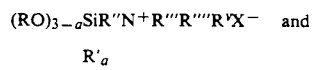

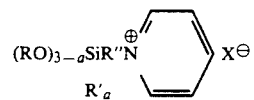

wherein in each formula R is an alkyl radical of 1 to 4 carbon atoms or hydrogen; a has a value of 0, 1 or 2; R' is a methyl or ethyl radical; R" is an alkylene group of 1 to 4 carbon atoms; R''', R'''' and R$^v$ are each independently selected from the group consisting of alkyl radicals of 1 to 18 carbon atoms, —CH$_2$C$_6$H$_5$, —CH$_2$CH$_2$OH, —CH$_2$OH, and —(CH$_2$)$_x$NHC(O)R$^{vi}$ wherein x has a value of from 2 to 10 and R$^{vi}$ is perfluoroalkyl radical having from 1 to 12 carbon atoms; and X is chloride, bromide, fluoride, iodide, acetate or tosylate.

6. The tampon of claim 5 wherein the organosilane is 3-(trimethoxysilyl) propyldimethyloctadecyl ammonium chloride of the formula

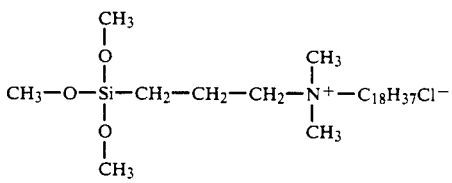

7. The tampon of claim 5 in which the polymer gel is in a form selected from the group consisting of flakes, strips, powders, filaments, or fibers.

8. The tampon of claim 5 in which the organosilane is present in the treated layer at a level of about ninety percent by weight based on the total weight of the treated layer.

* * * * *